United States Patent [19]

Krüger et al.

[11] Patent Number: 4,574,122

[45] Date of Patent: Mar. 4, 1986

[54] SUBSTITUTED O-ACYLGLYCOSYLAMIDES, PHARMACEUTICAL COMPOSITIONS AND METHOD OF USE

[75] Inventors: Bernd-Wieland Krüger, Wuppertal; Oswald Lockhoff, Cologne; Peter Stadler, Haan; Karl G. Metzger, Wuppertal, all of Fed. Rep. of Germany; Hans-Georg Opitz, Emeryville, Calif.; Klaus G. Stünkel, Wuppertal; Hans-Joachim Zeiler, Velbert, both of Fed. Rep. of Germany

[73] Assignee: Bayer Aktiengesellschaft, Leverkusen, Fed. Rep. of Germany

[21] Appl. No.: 675,690

[22] Filed: Nov. 28, 1984

[30] Foreign Application Priority Data

Dec. 7, 1983 [DE] Fed. Rep. of Germany ....... 3344257

[51] Int. Cl.$^4$ .................. A61K 31/70; C07H 5/06
[52] U.S. Cl. .................. 514/42; 536/18.7; 536/22; 536/53
[58] Field of Search ............ 536/18.7, 53, 22; 514/42

[56] References Cited

U.S. PATENT DOCUMENTS 2,612,497 9/1952 Meijer ..................... 536/53
3,843,799 10/1974 Elofson et al. .............. 536/22
4,025,622 5/1977 Ogura et al. ................ 536/22
4,066,750 1/1978 Smith et al. ................ 536/22

Primary Examiner—Johnnie R. Brown
Attorney, Agent, or Firm—Sprung, Horn, Kramer & Woods

[57] ABSTRACT

Compounds of the formula

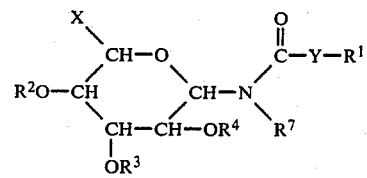

in which
X is hydrogen or the radical $-CH_2OR^5$,
three of $R^2$, $R^3$, $R^4$ and $R^5$ each independently is hydrogen or

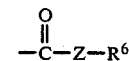

and the fourth is

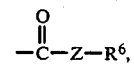

Z each independently is oxygen, sulphur, NH or $CH_2$, and
$R^1$, $R^6$ and $R^7$ each independently is an optionally substituted hydrocarbon radical having up to 50 carbon atoms,
stimulate the immune system's response and antibody production.

13 Claims, No Drawings

SUBSTITUTED O-ACYLGLYCOSYLAMIDES, PHARMACEUTICAL COMPOSITIONS AND METHOD OF USE

The present invention relates to compounds of the general formula I

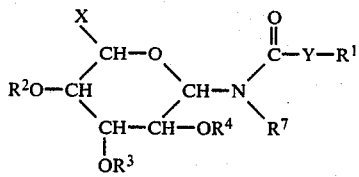

in which
X represents hydrogen or the radical —$CH_2OR^5$,
$R^2$, $R^3$, $R^4$ and $R^5$ are identical or different and represent hydrogen or the radical

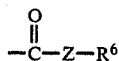

and Y and Z are identical or different and represent oxygen, sulphur, N—H or $CH_2$,
and wherein $R^1$, $R^6$ and $R^7$ are identical or different and represent an optionally substituted hydrocarbon radical having up to 50 carbon atoms, subject to the proviso that at least one of the radicals $R^2$, $R^3$, $R^4$ and $R^5$ denotes

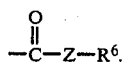

When the radicals $R^1$, $R^6$ or $R^7$ denote a hydrocarbon radical, this is understood, in accordance with the invention, to mean a linear or branched alkyl radical, a linear or branched, monounsaturated or polyunsaturated alkenyl radical, a saturated or unsaturated alicyclic radical or an aromatic radical (aryl). These meanings can also occur jointly within the same radical $R^1$, $R^6$ or $R^7$, that is to say, for example, in the form of alkylcycloalkyl, arylalkyl, alkylaryl, alkenylcycloalkyl, and the like.

It is also possible for individual methylene or methine groups in general up to 5, preferably 1, 2 or 3, to be replaced by O, S and/or N in the radicals $R^1$, $R^6$ and $R^7$. If the chain is interrupted by N, this nitrogen carries either H or a $C_1$-$C_{20}$-alkyl radical or an —CO—alkyl radical, and this alkyl group has 1-20 C atoms.

Preferably, $R^1$, $R^6$ and $R^7$ optionally represent alkyl or alkenyl radicals having 1 to 21 carbon atoms, preferably having 9 to 21 C atoms. Examples of saturated radicals which may be mentioned here are methyl, ethyl, propyl, i-propyl, butyl, i-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, docosyl, ethyl-pentyl, methyldecyl, i-propyldecyl, methyltridecosyl, eicosyl, tetracosyl, triacontyl, pentahexadecyl, 1-dodecylhexadecyl, 2-dodecylhexadecyl, 3-dodecylhexadecyl, 1-hexadecyloctadecyl, 2-hexadecyloctadecyl, 3-hexadecyloctadecyl, 4-hexadecyloctadecyl, 1-octadecyleicosyl and 2-octadecyleicosyl.

Examples of unsaturated radicals are ethenyl, 1-propenyl, 2-propenyl, i-butenyl, 1-butenyl, 2-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-decenyl, 5-decenyl, 9-decenyl, 8-heptadecenyl, 1,3-butadienyl, 1,3-pentadienyl, 1,4-pentadienyl, 2,4-pentadienyl, 8,11-heptadecanedienyl and 8,11,14-heptadecanetrienyl. In general, the longer-chain, unsaturated radicals are preferred, in particular the monounsaturated or diunsaturated alkenyls having 9-21 C atoms.

The unsaturated hydrocarbon radicals can be in the form of pure cis- or trans-isomers or in the form of mixtures of isomers.

Examples of cycloalkyl which may be mentioned are cyclopentyl, cyclohexyl, decahydronaphthyl and adamantyl.

Examples of alkylcycloalkyl radicals which may be mentioned are methylcyclopentyl, ethylcyclopentyl, n-propylcyclopentyl, i-propylcyclopentyl, butylcyclopentyl octylcyclopentyl, methylcyclohexyl, ethylcyclohexyl, propylcyclohexyl, butylcyclohexyl, hexylcyclohexyl, decylcyclohexyl, cyclopentylmethyl, cyclopentylethyl, cyclopentylpropyl, cyclopentylbutyl, cyclopentylpentyl, cyclopentylhexyl, cyclopentyloctyl, cyclopentyldecyl, cyclohexylmethyl, cyclohexylethyl, cyclohexylpropyl, cyclohexylbutyl, cyclohexylhexyl, cyclohexyldecyl, cyclopentyl, cyclohexylethyl, cyclohexylcyclopentylethyl and cyclohexylcyclohexylethyl.

Examples of aryl which may be mentioned are phenyl, naphthyl and biphenyl.

Examples of aralkyl for $R^1$, $R^6$ or $R^7$ are aryllower alkyl, such as benzyl, phenethyl or phenylhexyl.

The radicals $R^1$, $R^6$ and $R^7$ can be substituted, in general monosubstituted to pentasubstituted and preferably monosubstituted to trisubstituted. Suitable substituents are preferably the following: halogen, preferably F, Cl or Br, amino, $C_1$-$C_6$-alkylamino, di-$C_1$-$C_6$-alkylamino, oxo, OH, $C_1$-$C_6$-alkoxy, SH, $C_1$-$C_6$-alkylthio, $C_1$-$C_6$-alkyl—COO and $C_1$-$C_6$-alkyl—CO—NH.

Examples of cases in which the hydrocarbon radicals $R^1$, $R^6$ and $R^7$ are interrupted by O, S and N or corresponding groups of atoms, or are substituted, for example, by groups containing these atoms or by halogen atoms, are methoxyethyl, ethoxyethyl, n-propoxyethyl, n-butoxyethyl, i-propoxyethyl, i-butoxyethyl, sec.-butoxyethyl, methoxyethoxyethyl, ethoxyethoxyethyl, propoxyethoxyethyl, i-propoxyethoxyethyl, n-butoxyethoxyethyl, i-butoxyethoxyethyl, sec.-butoxyethoxyethyl, methoxyethoxyethoxyethyl, ethoxyethoxyethoxyethyl, n-propoxyethoxyethoxyethyl, i-propoxyethoxyethoxyethyl, n-butoxyethoxyethoxyethyl, i-butoxyethoxyethoxyethyl and sec.-butoxyethoxyethoxyethyl if Y and/or Z represent oxygen, sulphur, N—H or $CH_2$; methoxyethoxy, ethoxyethoxy, n-propoxyethoxy, i-propoxyethoxy, b-butoxyethoxy, i-butoxyethoxy, sec.-butoxyethoxy, methoxyethoxyethoxy, ethoxyethoxyethoxy, n-propoxyethoxyethoxy, i-propoxyethoxyethoxy, n-butoxyethoxyethoxy, i-butoxyethoxyethoxy and sec.-butoxyethoxyethoxy if Y and/or Z represent $CH_2$; or hydroxyheptadecenyl, oxobutyl or the aminodecyl, N-methylaminodecyl, fluoromethyl, β-hydroxytridecyl or mercaptoethyl radical.

The compounds of the formula I contain several chiral C atoms and exist as optically pure diastereomers or mixtures of diastereomers.

The compounds, according to the invention, of the formula I are thus carboxamides or N-alkylated or N- aralkylated carboxamides or carbamic acid, thiocarbamic acid or urea derivatives which additionally carry, at the nitrogen atom substituted by the abovementioned radical $R^7$, a simple monosaccharide radical which is attached as an N-glycoside, that is to say via the anomeric carbon atom, one or more hydroxyl groups in the saccharide radical being provided with an acyl, alk(aryl)oxycarbonyl, alkyl(aryl)thiocarbonyl or carbamoyl radical.

Compounds which are particularly preferred are those in which only one of the radicals $R^2$, $R^3$, $R^4$ or $R^5$ denotes

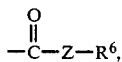

subject to the proviso that the other radicals $R^2$, $R^3$, $R^4$ and/or $R^5$ represent hydrogen and that $R^6$ and Z have the meaning mentioned above.

Compounds which are very particularly preferred are those in which $R^2$, $R^3$ and $R^4$ represent hydrogen and $R^5$ represents the radical

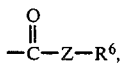

Z and $R^6$ having the meaning mentioned above.

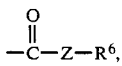

The following may be mentioned as examples:

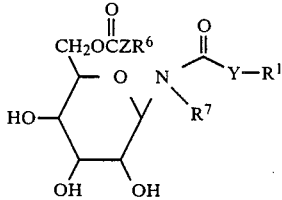

| Y | Z | R¹ | R⁶ | R⁷ |
|---|---|---|---|---|
| CH₂ | CH₂ | (CH₂)₉CH₃ | H | (CH₂)₁₁CH₃ |
| " | " | " | " | (CH₂)₁₃CH₃ |
| " | " | " | " | (CH₂)₁₅CH₃ |
| " | " | " | " | (CH₂)₁₇CH₃ |
| " | " | " | OCH₃ | (CH₂)₁₁CH₃ |
| " | " | " | " | (CH₂)₁₃CH₃ |
| " | " | " | " | (CH₂)₁₅CH₃ |
| " | " | " | " | (CH₂)₁₇CH₃ |
| O | " | " | H | (CH₂)₁₁CH₃ |
| " | " | " | " | (CH₂)₁₃CH₃ |
| " | " | " | " | (CH₂)₁₅CH₃ |
| " | " | " | " | (CH₂)₁₇CH₃ |
| " | " | " | OCH₃ | (CH₂)₁₁CH₃ |
| " | " | " | " | (CH₂)₁₃CH₃ |
| " | " | " | " | (CH₂)₁₅CH₃ |
| " | " | " | " | (CH₂)₁₇CH₃ |
| CH₂ | " | (CH₂)₁₁CH₃ | H | (CH₂)₁₁CH₃ |
| " | " | " | " | (CH₂)₁₃CH₃ |
| " | " | " | " | (CH₂)₁₅CH₃ |
| " | " | " | " | (CH₂)₁₇CH₃ |
| " | " | " | OCH₃ | (CH₂)₁₁CH₃ |
| " | " | " | " | (CH₂)₁₃CH₃ |
| " | " | " | H | (CH₂)₁₅CH₃ |
| " | " | " | " | (CH₂)₁₇CH₃ |
| O | " | " | " | (CH₂)₁₁CH₃ |
| " | " | " | " | (CH₂)₁₃CH₃ |
| " | " | " | " | (CH₂)₁₅CH₃ |
| " | " | " | " | (CH₂)₁₇CH₃ |

-continued

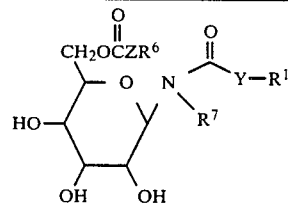

| Y | Z | R¹ | R⁶ | R⁷ |
|---|---|---|---|---|
| " | " | " | OCH₃ | (CH₂)₁₁CH₃ |
| " | " | " | " | (CH₂)₁₃CH₃ |
| " | " | " | " | (CH₂)₁₅CH₃ |
| " | " | " | " | (CH₂)₁₇CH₃ |
| CH₂ | " | (CH₂)₁₃CH₃ | H | (CH₂)₁₁CH₃ |
| " | " | " | " | (CH₂)₁₃CH₃ |
| " | " | " | " | (CH₂)₁₅CH₃ |
| " | " | " | " | (CH₂)₁₇CH₃ |
| " | " | " | OCH₃ | (CH₂)₁₁CH₃ |
| " | " | " | " | (CH₂)₁₃CH₃ |
| " | " | " | " | (CH₂)₁₅CH₃ |
| " | " | " | " | (CH₂)₁₇CH₃ |
| O | " | " | H | (CH₂)₁₁CH₃ |
| " | " | " | " | (CH₂)₁₃CH₃ |
| " | " | " | " | (CH₂)₁₅CH₃ |
| " | " | " | " | (CH₂)₁₇CH₃ |
| " | " | " | OCH₃ | (CH₂)₁₁CH₃ |
| " | " | " | " | (CH₂)₁₃CH₃ |
| " | " | " | " | (CH₂)₁₅CH₃ |
| " | " | " | " | (CH₂)₁₇CH₃ |
| CH₂ | " | (CH₂)₁₅CH₃ | H | (CH₂)₁₁CH₃ |
| " | " | " | " | (CH₂)₁₃CH₃ |
| " | " | " | " | (CH₂)₁₅CH₃ |
| " | " | " | " | (CH₂)₁₇CH₃ |
| " | " | " | OCH₃ | (CH₂)₁₁CH₃ |
| " | " | " | " | (CH₂)₁₃CH₃ |
| " | " | " | " | (CH₂)₁₅CH₃ |
| " | " | " | " | (CH₂)₁₇CH₃ |
| O | " | " | H | (CH₂)₁₁CH₃ |
| " | " | " | " | (CH₂)₁₃CH₃ |
| " | " | " | " | (CH₂)₁₅CH₃ |
| " | " | " | " | (CH₂)₁₇CH₃ |
| " | " | " | OCH₃ | (CH₂)₁₁CH₃ |
| " | " | " | " | (CH₂)₁₃CH₃ |
| " | " | " | " | (CH₂)₁₅CH₃ |
| " | " | " | " | (CH₂)₁₇CH₃ |
| CH₂ | " | (CH₂)₉CH₃ | OCH₂CH₂O—C₄H₉—n | (CH₂)₁₁CH₃ |
| " | " | " | OCH₂CH₂O—C₄H₉—n | (CH₂)₁₃CH₃ |
| " | " | " | OCH₂CH₂O—C₄H₉—n | (CH₂)₁₅CH₃ |
| " | " | " | OCH₂CH₂O—C₄H₉—n | (CH₂)₁₇CH₃ |
| " | " | (CH₂)₁₁CH₃ | OCH₂CH₂O—C₄H₉—n | (CH₂)₁₁CH₃ |
| " | " | " | OCH₂CH₂O—C₄H₉—n | (CH₂)₁₃CH₃ |
| " | " | " | OCH₂CH₂O—C₄H₉—n | (CH₂)₁₅CH₃ |
| " | " | " | OCH₂CH₂O—C₄H₉—n | (CH₂)₁₇CH₃ |
| " | " | (CH₂)₁₃CH₃ | OCH₂CH₂O—C₄H₉—n | (CH₂)₁₁CH₃ |
| " | " | " | OCH₂CH₂O—C₄H₉—n | (CH₂)₁₁CH₃ |
| " | " | " | OCH₂CH₂O—C₄H₉—n | (CH₂)₁₃CH₃ |
| " | " | " | OCH₂CH₂O—C₄H₉—n | (CH₂)₁₅CH₃ |
| " | " | (CH₂)₁₅CH₃ | OCH₂CH₂O—C₄H₉—n | (CH₂)₁₁CH₃ |
| " | " | " | OCH₂CH₂O—C₄H₉—n | (CH₂)₁₃CH₃ |
| " | " | " | OCH₂CH₂O—C₄H₉—n | (CH₂)₁₅CH₃ |
| " | " | " | OCH₂CH₂O—C₄H₉—n | (CH₂)₁₇CH₃ |

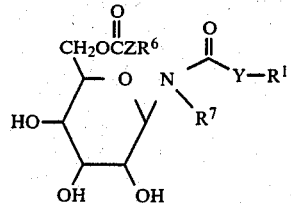

| Y | Z | R¹ | R⁶ | R⁷ |
|---|---|---|---|---|
| " | " | $(CH_2)_9CH_3$ | $(OCH_2CH_2)_2OC_4H_{9-n}$ | $(CH_2)_{11}CH_3$ |
| " | " | " | $(OCH_2CH_2)_2OC_4H_{9-n}$ | $(CH_2)_{13}CH_3$ |
| " | " | " | $(OCH_2CH_2)_2OC_4H_{9-n}$ | $(CH_2)_{15}CH_3$ |
| " | " | " | $(OCH_2CH_2)_2OC_4H_{9-n}$ | $(CH_2)_{17}CH_3$ |
| " | " | $(CH_2)_{11}CH_3$ | $(OCH_2CH_2)_2OC_4H_{9-n}$ | $(CH_2)_{11}CH_3$ |
| " | " | " | $(OCH_2CH_2)_2OC_4H_{9-n}$ | $(CH_2)_{13}CH_3$ |
| " | " | " | $(OCH_2CH_2)_2OC_4H_{9-n}$ | $(CH_2)_{15}CH_3$ |
| " | " | " | $(OCH_2CH_2)_2OC_4H_{9-n}$ | $(CH_2)_{17}CH_3$ |
| " | " | $(CH_2)_{13}CH_3$ | $(OCH_2CH_2)_2OC_4H_{9-n}$ | $(CH_2)_{11}CH_3$ |
| " | " | " | $(OCH_2CH_2)_2OC_4H_{9-n}$ | $(CH_2)_{13}CH_3$ |
| " | " | " | $(OCH_2CH_2)_2OC_4H_{9-n}$ | $(CH_2)_{15}CH_3$ |
| " | " | " | $(OCH_2CH_2)_2OC_4H_{9-n}$ | $(CH_2)_{17}CH_3$ |
| " | " | $(CH_2)_{15}CH_3$ | $(OCH_2CH_2)_2OC_4H_{9-n}$ | $(CH_2)_{11}CH_3$ |
| " | " | " | $(OCH_2CH_2)_2OC_4H_{9-n}$ | $(CH_2)_{13}CH_3$ |
| " | " | " | $(OCH_2CH_2)_2OC_4H_{9-n}$ | $(CH_2)_{15}CH_3$ |
| " | " | " | $(OCH_2CH_2)_2OC_4H_{9-n}$ | $(CH_2)_{17}CH_3$ |
| " | " | $(CH_2)_9CH_3$ | $(OCH_2CH_2)_2OC_4H_{9-n}$ | $(CH_2)_{11}CH_3$ |
| " | " | " | " | $(CH_2)_{13}CH_3$ |
| " | " | " | $(OCH_2CH_2)_2OC_4H_{9-n}$ | $(CH_2)_{15}CH_3$ |
| " | " | " | $(OCH_2CH_2)_2OC_4H_{9-n}$ | $(CH_2)_{15}CH_3$ |
| " | " | $(CH_2)_{11}CH_3$ | $(OCH_2CH_2)_2OC_4H_{9-n}$ | $(CH_2)_{11}CH_3$ |
| " | " | " | $(OCH_2CH_2)_2OC_4H_{9-n}$ | $(CH_2)_{13}CH_3$ |
| " | " | " | $(OCH_2CH_2)_2OC_4H_{9-n}$ | $(CH_2)_{15}CH_3$ |
| " | " | " | $(OCH_2CH_2)_2OC_4H_{9-n}$ | $(CH_2)_{17}CH_3$ |

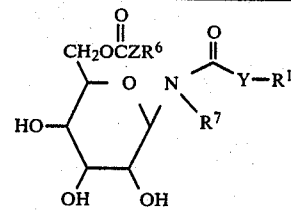

| Y | Z | R¹ | R⁶ | R⁷ |
|---|---|---|---|---|
| " | " | $(CH_2)_{13}CH_3$ | $(OCH_2CH_2)_2OC_4H_{9-n}$ | $(CH_2)_{11}CH_3$ |
| " | " | " | $(OCH_2CH_2)_2OC_4H_{9-n}$ | $(CH_2)_{13}CH_3$ |
| " | " | " | $(OCH_2CH_2)_2OC_4H_{9-n}$ | $(CH_2)_{15}CH_3$ |
| " | " | " | $(OCH_2CH_2)_2OC_4H_{9-n}$ | $(CH_2)_{17}CH_3$ |
| " | " | $(CH_2)_{15}CH_3$ | $(OCH_2CH_2)_2OC_4H_{9-n}$ | $(CH_2)_{11}CH_3$ |
| " | " | " | $(OCH_2CH_2)_2OC_4H_{9-n}$ | $(CH_2)_{13}CH_3$ |
| " | " | " | $(OCH_2CH_2)_2OC_4H_{9-n}$ | $(CH_2)_{15}CH_3$ |
| " | " | " | $(OCH_2CH_2)_2OC_4H_{9-n}$ | $(CH_2)_{17}CH_3$ |
| " | O | $(CH_2)_9CH_3$ | $(CH_2CH_2O)_2-C_2H_5$ | $(CH_2)_{11}CH_3$ |
| " | " | " | $(CH_2CH_2O)_2-C_2H_5$ | $(CH_2)_{13}CH_3$ |
| " | " | " | $(CH_2CH_2O)_2-C_2H_5$ | $(CH_2)_{15}CH_3$ |
| " | " | " | $(CH_2CH_2O)_2-C_2H_5$ | $(CH_2)_{17}CH_3$ |
| " | " | $(CH_2)_{11}CH_3$ | $(CH_2CH_2O)_2-C_2H_5$ | $(CH_2)_{17}CH_3$ |
| " | " | " | $(CH_2CH_2O)_2-C_2H_5$ | $(CH_2)_{13}CH_3$ |
| " | " | " | $(CH_2CH_2O)_2-C_2H_5$ | $(CH_2)_{15}CH_3$ |
| " | " | " | $(CH_2CH_2O)_2-C_2H_5$ | $(CH_2)_{17}CH_3$ |
| " | " | $(CH_2)_{13}CH_3$ | $(CH_2CH_2O)_2-C_2H_5$ | $(CH_2)_{11}CH_3$ |
| " | " | " | $(CH_2CH_2O)_2-C_2H_5$ | $(CH_2)_{13}CH_3$ |
| " | " | " | $(CH_2CH_2O)_2-C_2H_5$ | $(CH_2)_{15}CH_3$ |
| " | " | " | $(CH_2CH_2O)_2-C_2H_5$ | $(CH_2)_{17}CH_3$ |
| " | " | $(CH_2)_{15}CH_3$ | $(CH_2CH_2O)_2-C_2H_5$ | $(CH_2)_{11}CH_3$ |
| " | " | " | $(CH_2CH_2O)_2-C_2H_5$ | $(CH_2)_{13}CH_3$ |
| " | " | " | $(CH_2CH_2O)_2-C_2H_5$ | $(CH_2)_{15}CH_3$ |
| " | " | " | $(CH_2CH_2O)_2-C_2H_5$ | $(CH_2)_{17}CH_3$ |

The invention also relates to a process for the preparation of the compounds of the formula I.

In this process, compounds of the formula II

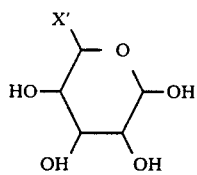

(II)

in which

X' represents hydrogen or —CH$_2$OH are reacted, either in the free, that is to say unprotected, form or in the form of protected and, if appropriate, activated derivatives, initially with an amino compound R$^7$—NH$_2$, either in the free form or in the form of a suitable acid addition salt, R$^7$ having the meaning described above, and the glycosylamine thus obtained is then acylated with a carboxylic acid, carbonic acid or thiocarbonic acid derivative or isocyanate which is—as is customary in acylation reactions—activated and is, if appropriate, protected at functional groups, protective groups which may be present in the reaction product then obtained are split off selectively or entirely, and, in a second process stage, the intermediate product thus obtained which is free, that is to say unprotected, at at least one hydroxyl group is reacted with a carboxylic acid, carbonic acid or thiocarbonic acid derivative or isocyanate which is—as is customary in acylation reactions—activated and is, if appropriate, protected at functional groups. After protective groups which may optionally be present have been split off, the compounds, according to the invention, of the formula I are obtained in this manner and can, if necessary, be purified by chromatography, recrystallization, extraction or similar means.

In a preferred embodiment of the process according to the invention, the unblocked sugar of the formula II is reacted, in a manner which is in itself known, in a first process stage, with 1 to 10 equivalents of the appropriate amine R$^7$—NH$_2$ in a suitable solvent, or in the absence of a solvent, if appropriate in the presence of a catalyst and at temperatures between 0° C. and 80° C., and the appropriate glycosylamines are obtained after working up, usually in high yields, in the form of amorphous or crystalline solids or in the form of viscous syrups.

In the second process stage, the glycosylamine is then reacted with 1 to 10 equivalents of an acyl derivative of the formula R$_1$—Y—CO—X'' in which R$_1$ and Y have the abovementioned meaning and X'' denotes halogen or a leaving group which is customary in acylation reactions, preferably an activating ester radical or a group O—OC—Y—R$_1$ in which Y and R$_1$ have the above meaning, or with 1 to 10 equivalents of an isocyanate of the formula R$^1$—NCO, the reaction being carried out in an organic or aqueous organic solvent at temperatures between −30° C. and 80° C. and, if appropriate, in the presence of a base, and the reaction product being worked up in a customary manner when the reaction is complete.

In the third process stage, the derivative thus obtained, which has been reacted at the nitrogen, is reacted, in a protected or unprotected form, with 1 to 10 equivalents of an acyl derivative of the formula

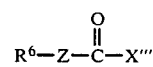

in which

R$^6$ and Z have the abovementioned meaning and

X''' denotes halogen or a leaving group which is customary in acylation reactions, preferably an activating ester radical, or a group

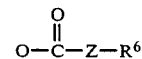

in which

R$^6$ and Z have the abovementioned meaning or with 1 to 10 equivalents of an isocyanate of the formula R$^6$—NCO, the reaction being carried out in an organic or aqueous organic solvent at temperatures between −30° C. and 80° C. and, if appropriate, in the presence of a base, and the reaction product being worked up in a customary manner when the reaction is complete.

The first process stage in the preparation of the compounds, according to the invention, of the formula I is thus the reaction of a sugar with an amine of the type R$^7$—NH$_2$ at the anomeric carbon atom, with the elimination of water, to give the appropriate glycosylamine.

Amines R$^7$—NH$_2$ which are liquid at room temperature can be reacted with the sugar in a direct manner, that is to say without solvent. This reaction is carried out at temperatures between 0° C. and 100° C., preferably at 25° C. to 70° C. Suitable catalysts are mineral acids, such as, for example, hydrochloric acid, sulphuric acid or nitric acid, or short-chain carboxylic acids, such as acetic acid or propionic acid; these are employed in amounts of 0.001 to 0.05 equivalent.

It is possible in every case, and also preferable in the case of amines R$^7$—NH$_2$ which are solid at room temperature, to carry out the preparation of the glycosylamines in the presence of a solvent. The reaction is then preferably carried out in the presence of a diluent which is inert under the reaction conditions and which is preferably so constituted that, at the least, either the reactants or the reaction product dissolve in it.

Suitable diluents are alcohols, such as methanol, ethanol, 1-propanol and 2-propanol, ethers, such as tetrahydrofuran and dioxane, and also dimethylformamide, and—except in the event that alcohols are used—the addition of water is preferable. In addition, water on its own is also preferentially suitable as the solvent in the case of short-chain amines R$^7$—NH$_2$. It can also be advantageous to use the alcohols in the form of a mixture with water.

When solvents are used in the preparation of the glycolsylamines, the reaction temperatures are between −10° C. and 120° C., preferably between 30° C. and 70° C.

The diluent concerned can be added before or during the reaction, as desired. In the case of long-chain amines R$^7$—NH$_2$, addition before the reaction is to be preferred.

The glycosylamines which have been prepared as described above crystallize either without further treatment or after cooling, and can be precipitated or induced to crystallize by adding suitable auxiliary solvents, preferably auxiliary solvents of lower polarity, such as acetone, diethyl ether, cyclohexane, ethyl acetate or petroleum ether, if appropriate with cooling; excess amine $R^7$—$NH_2$ which may be present can be removed by washing or recrystallizing the product in a manner which is in itself known.

The second process stage in the preparation of the compounds, according to the invention, of the formula I is the selective N-acylation of a glycosylamine obtained as described above by means of an acyl derivative of the formula $R_1$—Y—CO—X″ in which $R_1$, Y and X″ have the meaning indicated above, or by means of an isocyanate of the formula $R_1$—NCO.

The third process stage in the preparation of the compounds, according to the invention, of the formula I is the selective O-acylation of a protected or unprotected N-acylated aminoglycoside, described above, by means of an acyl derivative of the formula

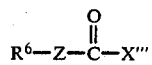

in which
$R^6$, Z and X‴ have the meaning indicated above, or by means of an isocyanate of the formula $R^6$—NCO.

Preferred carboxyl derivatives $R_1$—Y—CO—X″ or

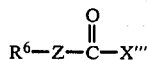

which are in themselves known are anhydrides, activated esters and acid halides, preferably chlorides.

These compounds are preferably reacted with the glycosylamines in the presence of a diluent in which the reactants are completely or only partly dissolved.

Organic or inorganic solvents are suitable, preferably those which as far as possible reduce or prevent side reactions under the reaction conditions. The reaction can be carried out either in organic solvents, such as ethers, for example tetrahydrofuran and dioxane, or alcohols, for example ethanol and propanol, or ketones, for example acetone or methyl ethyl ketone, or in dimethylformamide, ethyl acetate or pyridine and also in mixtures of these solvents with one another and/or with water. In general, the use of anhydrous solvents is to be preferred.

The compounds $R^1$—Y—COX″/$R^6$ZCO—X‴ or $R^1$—NCO/$R^6$—NCO are employed in 1 to 10 equivalents, relative to the glycosylamine/glcosylamide, respectively.

If acid halides and anhydrides are used, the reactions can preferably be carried out in the presence of basic auxiliaries. It is possible to use any of the basic compounds customary in organic synthesis, such as, for example, tertiary aliphatic or aromatic amines or alkali or alkaline earth metal hydroxides or carbonates, such as sodium hydroxide solution, sodium carbonate or calcium carbonate.

The reactions are carried out at temperatures between about $-30°$ C. and $+80°$ C., preferably between $-10°$ C. and $+20°$ C.

In cases where a selective reaction of a hydroxyl group cannot be carried out, either because a less reactive secondary hydroxyl group of the sugar residue is to be reacted with the radical

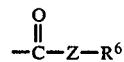

in which
Z and $R^6$ have the abovementioned meaning, in the presence of a more reactive primary hydroxyl group, or because a secondary hydroxyl group is to be reacted with the radical

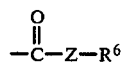

in a selective manner in the presence of other secondary hydroxyl groups, the actual acylation reaction must be preceded by a series of protective group operations in which the hydroxyl group which is to be reacted selectively with the radical

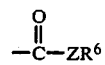

is in a free, that is to say unsubstituted, form at the conclusion of the blocking reactions. The hydroxyl groups which are not to be reacted must, therefore, be blocked before the acylation reaction.

Suitable protective groups for sugar derivatives are described in the relevant literature (for example C. B. Reese, in "Protecting Groups in Organic Chemistry", 1973, pp. 95–143; Plenum Press). Any of the protective groups used in sugar chemistry and combinations thereof can be employed.

Examples of suitable protective groups are esters, such as acetyl, benzoyl, pivaloyl or p-methoxybenzoyl, ethers, such as benzyl, p-methoxybenzyl, allyl or 1-propenyl, alkylidene compounds, such as ethylidene, isopropylidene or benzylidene, orthoesters, such as 1-methoxyethylidene or 1-ethoxyethylidene, silyl ethers, such as trimethylsilyl or t.-butyldimethylsilyl, or organic metal compounds, such as boric acid esters or tin ethers or tin ketals, such as tributylstannyl or dibutylstannylidene.

The carbohydrate derivatives which have been blocked by these protective groups are then reacted with the group

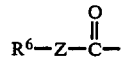

in a suitable solvent at the hydroxyl group(s) which is/are still free. Suitable solvents and suitable processes for the acylation are mentioned above.

The O-acylated amides, ureas, carbamates or thiocarbamates obtained in this manner are isolated by processes which are in themeselves known in the form of crystalline or amorphous solids or in the form of viscous syrups, and, if necessary, are purified by recrystallization, chromatography, extraction and the like.

In the case of compounds having protected hydroxyl groups in the glycosyl moiety, the protective groups can be split off in a manner which is in itself known.

The following reaction diagram is intended to illustrate in an exemplary manner one of the preferred embodiments of the preparation, according to the invention, of compounds of the formula I:

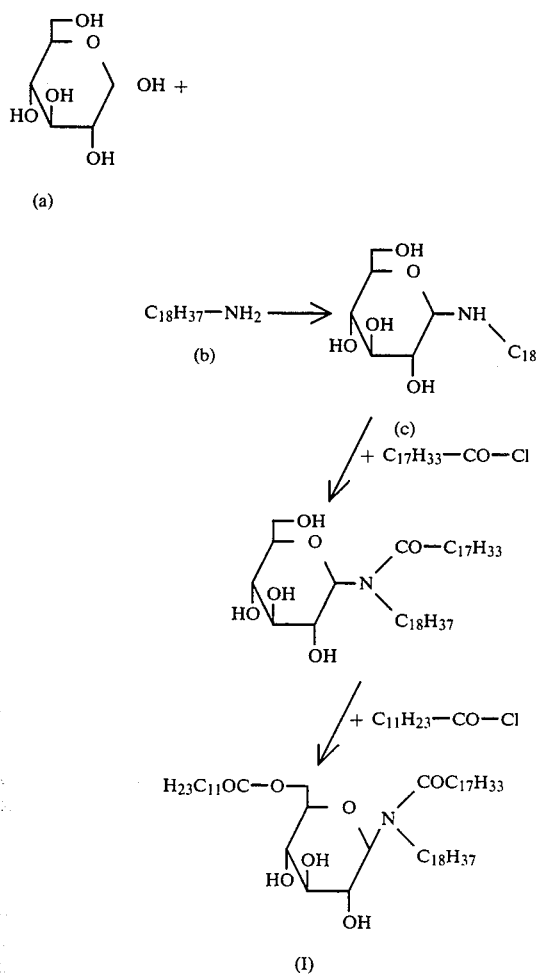

In the first process stage, glucose (a) is reacted with octadecylamine (b) to give N-octadecyl-β-D-glucopyranosylamine (c), which is acylated in the second process stage with oleyl chloride to give N-octadecyl-N-oleyl-β-D-glucopyranosylamine (d). In the third process stage, O-acylation is then carried out in position 6 by means of dodecanoyl chloride, and N-octadecyl-N-oleyl-(6-lauroyl-β-D-glucopyranosyl)-amide (I) is obtained.

The compounds of the present invention have a pronounced effect increasing the defenses. It has been found that the class of compounds increases, in an antigen-specific manner, the synthesis of antibodies by the immune system, and moreover strengthens the non-specific defenses inherent to the host. These results were obtained using the following designs of experiments.

Increase in the Primary Humoral Immunity toward Sheep Erythrocytes (SE) in vitro.

It is possible experimentally to induce in vitro the development of a humoral immune response with heterologous red blood cells by primary immunization of mouse spleen cells in suspension cultures (R. I. Mishell and R. W. Dutton, J. Exp. Med. 126, 423 (1967)). For this purpose, Balb/c mouse spleen cells were cultured for 5 days in the presence of antigen (SE) and the test substance. The cells are harvested, washed and plated out together with the antigen and complement in semi-solid agar, and incubated at 37° C. for 2 hours (N. K. Jerne, A. A. Nordin and C. Henry, "Cell bound Antibodies", eds. Amos and Koprowski, Wistar Inst. Press, Philadelphia, USA, pp. 109 (1963)). The antigen sensitization of mouse lymphocytes in the primary culture results in the synthesis and release of Ak. The specific antibodies which are secreted bind to the SE antigen and lyse these cells due to the presence of complement (plaque-formation). Substances of the present class of compounds (for example those of Examples 8, 9, 10 and 12) are capable of increasing, in a dose-dependent manner in the range 3 to 100 μl/ml, the number of antibody-forming cells.

Increase in the Primary Humoral Immunity toward the Soluble Antigen Ovalbumin in vivo.

NMRI mice were immunized subcutaneously (s.c.) with a suboptimal dose of antigen (1 μg/animal, day 0). When the antigenic stimulation was suboptimal, only a small number of lymphocytes in the animals were stimulated to synthesize antibodies. Additional treatment of the animals with, for example, the compounds of Examples 8 and 12 according to the invention, is able to increase significantly the antibody titre in the serum of the animals on a single subcutaneous administration of 3 to 30 mg/kg.

The antibody titre was determined by indirect haemagglutination on day 10. The effect of the treatment is expressed by the geometric mean of $Log_2$ of the titre.

The immunostimulant effect of the compounds mentioned is, in contrast to other immunostimulants, for example those from bacteria, such as LPS from Gram-negative bacteria, dependent on the antigen, that is to say the substances surprisingly induce antibody synthesis only when combined with an antigenic stimulus (in this instance SE or ovalbumin). In contrast to the conventional immunostimulants mentioned, they have no mitogenic properties.

Tolerability

Although compounds of the type described display their potentiating effect on the mouse after, for example, a single dose of only 10 mg/kg i.p. or orally, no toxic effects are observed even on administration of 100 mg/kg. Thus the substances mentioned have good tolerability.

The compounds according to the invention have the ability of, on the one hand when mixed with an antigen, of increasing its immunogenicity and, on the other hand on systemic administration, of increasing the immunological responsiveness of the treated organism. At the same time, the substances mentioned are capable of activating the lymphocytes responsible for the formation of antibodies. The new compounds can thus be used as adjuvants mixed with vaccines to increase the success of vaccination and to increase the protection from infection provided by the immunity to bacterial, viral or parasitic pathogens.

Moreover, the compounds described are suitable as adjuvants, when mixed with a wide variety of antigens, for the experimental and industrial production of antisera for therapy and diagnosis.

Furthermore, the new compounds can be used, even without simultaneous administration of antigen, to promote defense responses which are already taking place at a subthreshold level in humans and animals. Accordingly, the compounds are particularly suitable for stimulation of the body's own defense mechanism, for example where there are chronic and acute infections or selective (antigen-specific) immunological deficiencies, and for congenital as well as acquired general (that is to say not antigen-specific) states of immunological deficiency as occur in the elderly, during the course of severe primary diseases and, in particular, following therapy with ionizing radiation or with compounds having immunosuppressive activity. The compounds mentioned can thus preferably be administered combined with anti-infectious antibiotics, chemotherapeutic agents or other remedial procedures in order to counteract immunological damage. Finally, the compounds mentioned are also suitable for the general prophylaxis of infectious diseases in humans and animals.

The compounds according to the invention increase the survival rate in the animal model of acute and chronic bacterial infection.

DESCRIPTION OF THE EXPERIMENT

The compounds according to the invention can be used alone as a prophylactic agent to combat existent infections, or they can be used combined with antibiotic therapy to increase the therapeutic effect of antibiotics and chemotherapeutic agents (for example penicillins, cephalosporins, aminoglycosides etc.) in infected humans and animals.

It has been found that therapy of infections of the mouse with pathogenic organisms which lead to the death of the experimental animals within 24 to 28 hours is possible by prophylactic treatment, preferably intraperitoneally, with 1 to 80 mg/kg of, for example, the compounds of Examples 9, 10 and 12 according to the invention. This applies to a large number of Gram-positive (for example Staphylococci) and Gram-negative (for example E. coli, Klebsiella, Proteus and Pseudomonas) pathogens. This list is by way of example and is not to be interpreted as restrictive in any manner. Thus, for example, 40 to 100% of mice which have been infected with the phathogenic strain Klebsiella 63 survive this infection after treatment (for example 18 hours before infection) with 10 to 40 mg/kg of the compound according to the invention, while only 0 to 30% of the untreated control animals survived.

It was shown, in another model experiment, that the therapeutic efficacy of antibiotics can be increased by the compounds according to the invention. Thus, mice were infected with the strain Pseudomonas W. This infection led to the death of most of the control animals within 24 hours.

Another group was treated with 4 mg/kg sisomycin 30 hours after infection. It was shown that it was possible significantly to improve the therapeutic efficacy of the sisomycin in the experimental group which had been treated with the compounds according to the invention 18 hours before infection.

The pharmaceutical products of the present invention are preferably tablets or gelatine capsules which contain the active compounds together with diluents, for example, lactose, dextrose, sucrose, mannitol, sorbitol, cellulose and/or lubricants, for example diatomaceous earth, talc, stearic acid or salts thereof, such as magnesium or calcium stearate and/or polyethylene glycol. Tablets additionally contain binders, for example magnesium aluminum, silicate, starches, such as corn wheat, rice, or arrowroot starch, gelatin, tragacanth, methylcellulose, sodium carboxymethylcellulose and/or polyvinylpyrrolidone and, if desired, disintegrants, for example starches, agar, alginic acid or a salt thereof, such as sodium alginate and/or effervescent mixtures, or adsorption agents, colorants, flavorings and sweeteners.

Injectable products are preferably isotonic aqueous solutions or suspensions. Suppositories, ointments or creams are primarily fatty emulsions or suspensions. The pharmaceutical products can be sterilized and/or contain auxiliaries, for example preservatives, stabilizers, wetting and/or emulsifying agents, solubilizers, salts to control the osmotic pressure and/or buffers. The present pharmaceutical products which, if desired, can contain other compounds of pharmacological value, are produced in a manner known per se, for example by conventional mixing, granulating or coating processes, and they contain from about 0.1% to about 75%, in particular from about 1% to 50%, of the active compounds mentioned.

The products of the present invention for oral administration can also be provided with a coating which is resistant to gastric juice.

The compounds according to the invention can be used as agents increasing the defences and as immunopotentiating agents for the treatment of chronic and acute infections (for example bacterial, viral and parasitic). They can likewise be used as adjuvants for vaccination, for the stimulation of phagocytosis, and where there is dysregulation of the defense and immune systems.

EXAMPLES

Example 1

N-Octadecyl-D-glucopyranosylamine 20 g of octadecylamine are dissolved in 120 ml of ethanol and the solution is warmed to 70° C. 11 g of anhydrous D-glucose are added. Stirring is continued for a further 15 minutes at 70° after a clear solution has been formed. The mixture is cooled to 10° and allowed to stand for 15 minutes. The resulting mash of crystals is filtered off with suction, washed twice with ethanol and dried in vacuo.

Elementary analysis: Calculated: C 66.8% H 11.4% N 3.2%. Found: C 67.4% H 11.8% N 3.7%.

Example 2

N-Glucopyranosyl-N-octadecyldodecanamide 10 g of the compound from Example 1 are suspended in 20 ml of tetrahydrofuran, 10 g of sodium carbonate are added and 10 g of dodecanoyl chloride in 10 ml of tetrahydrofuran are then added dropwise. When the reaction is complete (checked by thin layer chromatography on silica gel 60 6:1 toluene/isopropanol), the solid is filtered off, the filtrate is evaporated in vacuo to a syrup, and the crude product is purified by column chromatography on silica gel 60 using 10:1 toluene/isopropanol as the mobile phase.

$a_D = 8°$ (c=1.0 in dioxane).

Example 3

N-Dodecyl-D-galactopyranosylamine

Prepared in accordance with Example 1 from D-galactose and dodecylamine.

Elementary analysis: Calculated: C 62.2% H 10.7% N 4.0%. Found: C 62.5% H 10.2% N 4.4%.

Example 4

N-Galactopyranosyl-N-dodecyloctadecanamide

Prepared in accordance with Example 2 from 10 g of the compound according to Example 3 and 16 g of stearoyl chloride.

$\alpha_D = 4.4°$ (c=1.0 in methylene dichloride). Rf value=0.23 in 4:1 toluene/n-propanol.

Example 5

N-Octadecyl-N-(D-glucopyranosyl)-decylurethane 9 g of the compound from Example 1 were suspended in 160 ml of tetrahydrofuran and 40 ml of ethanol, and 9 g of sodium carbonate were added. 5 g of decyl chloroformate, dissolved in 40 ml of tetrahydrofuran, are added to this suspension dropwise in the course of 20 minutes. When the reaction is complete, the mixture is filtered and the filter residue is rinsed with tetrahydrofuran. The filtrate is combined with the wash solutions and evaporated in vacuo. The resulting syrup is purified by chromatography (mobile phase 20:1 methylene dichloride/methanol).

Rf value 0.37 in 10:1 $CH_2Cl_2/CH_3OH$.

Elementary analysis: Calculated: C 68.3% H 11.3% N 2.3%. Found: C 68.4% H 11.6% N 2.4%.

Example 6

N-Octadecyl-N-(D-glucopyranosyl)-N'-dodecylurea 9 g of the compound from Example 1 are suspended in 160 ml of tetrahydrofuran and 40 ml of ethanol. 4.3 g of dodecyl isocyanate, dissolved in 20 ml of tetrahydrofuran, are added dropwise to this suspension in the course of 20 minutes. When the reaction is complete, the mixture is evaporated in vacuo and the resulting syrup is purified by column chromatography (mobile phase 15:1 methylene dichloride/methanol).

Rf value: 0.33 in 10:1 $CH_2Cl_2/CH_3OH$. $\alpha_D = 7.4°$ (c=1.04 in dioxane).

Example 7

N-Octadecyl-lauroyl-4-(3,6-dioxodecoyl)-$\beta$-D-glucopyranosylamide 10 g (0.016 mol) of the compound from Example 2 are dissolved in 100 ml of tetrahydrofuran, 3.5 g of benzaldehyde dimethyl acetal and 10 mg of para-toluenesulphonic acid are added and the mixture is warmed at 70° C. for 1 hour. After cooling to room temperature, the mixture is neutralized with ion exchanger MP 500 (OH form) and concentrated in a high vacuum. The resulting syrup is taken up in 100 ml of tetrahydrofuran, 1.5 g of sodium hydride and 3.5 ml of benzyl bromide are added, and the mixture is warmed at 40° C. for 1 hour. After cooling to room temperature, 20 ml of methanol are added and the mixture is stirred for a further hour. 10 ml of water are added cautiously to the mixture, which is concentrated in a high vacuum. The resulting syrup is taken up in 100 ml of methylene dichloride, and the solution is extracted with twice 20 ml of water, dried over magnesium sulphate and concentrated in vacuo, and the residue is purified by column chromatography (mobile phase 20:1 toluene/ethyl acetate). The resulting syrup is dissolved in 30 ml of tetrahydrofuran, 30 ml of 10:1 glacial acetic acid/water are added, and the mixture is warmed at 70° for 1 hour, cooled to room temperature and evaporated several times with toluene in a high vacuum. The resulting syrup (7.8 g), which is a single substance in terms of chromatography, is dissolved in 100 ml of tetrahydrofuran, stirred with 400 mg of sodium hydride for 30 minutes at 50° and cooled to 0° and 1.8 g of benzyl bromide are added. After 3 hours the mixture is warmed to room temperature and stirring is continued overnight. 5 ml of methanol are added and the mixture is stirred for a further hour, water is then added cautiously and the mixture is evaporated. The residue obtained is taken up in methylene dichloride and water, and the organic phase is extracted with water, dried and concentrated in a high vacuum. The residue is taken up in 100 ml of tetrahydrofuran, and a freshly prepared solution—in tetrahydrofuran—of 0.018 mol of the mixed anhydride formed from ethyl chloroformate and 3,6-dioxodecanoic acid is added to the solution.

The reaction mixture is stirred for 12 hours at 20° C. and filtered, and the filtrate is evaporated in vacuo to give a syrup, which is then purified by column chromatography (10:1 petroleum ether/THF).

The main product obtained is dissolved in 80 ml of tetrahydrofuran and 10 ml of glacial acetic acid and is hydrogenated in the presence of 2 g of palladium-on-charcoal. When the absorption of hydrogen is complete, the catalyst is filtered off, the filtrate is evaporated in vacuo to give a syrup and the latter is evaporated several times with toluene.

Elementary analysis: Calculated: C 68.44% H 11.10% N 1.81%. Found: C 68.3% H 10.9% N 1.8%.

Example 8

N-Octadecyl-N-3,6-dioxodecoyl-(6-stearyl-$\beta$-D-glucopyranosyl)-amine 1.2 g (0.004 mol) of octadecanoyl chloride and 2.0 g (0.0034 mol) of N-octadecyl-N-3,6-dioxodecanoyl-$\beta$-D-glucopyranosylamine in 50 ml of tetrahydrofuran are initially taken, and 0.4 g of triethylamine (0.004 mol) is added at 0° C. The mixture is stirred for 1 day at 20° C., the solid is filtered off with suction and the solvent is removed in a water-pump vacuum. The residue is chromatographed on a column containing 250 g of silica gel, using as mobile phase 10:1 toluene/isopropanol, and 1.9 g (65% of theory) of N-octadecyl-N-3,6-dioxodecoyl-(6-stearyl-$\beta$-D-glucopyranosyl)-amine are obtained, having an Rf value of 0.296 (6:1 toluene/isopropanol).

Example 9

N-Octadecyl-N-stearyl-6-[(2,2-dimethylpropyl)-aminocarbonyl]-$\beta$-D-glucopyranosylamine 0.7 g (0.0063 mol) of neopentyl isocyanate, dissolved in 20 ml of tetrahydrofuran, are added at 20°, in the course of one hour, to 3.1 g (0.005 mol) of N-octadecyl-N-lauroyl-$\beta$-D-glucopyranosylamide and 20 ml of DABCO in 40 ml of tetrahydrofuran. The mixture is stirred for 1 day at 20° C. and a further 0.2 g of isocyanate are added in order to complete the reaction. After stirring at 20° C. for 2 days, volatile constituents are removed under a water-pump vacuum, and the residue is chromatographed over 200 g of silica gel (mobile phase 10:1 toluene/isopropanol). 1.4 g (39% of theory) of N-octadecyl-N-lauroyl-6-[(2,2-dimethylpropyl)-aminocarbonyl[-$\beta$-D-glucopyranosylamine are obtained, having an Rf value of 0.34 (6:1 toluene/isopropanol).

The following are obtained analogously:

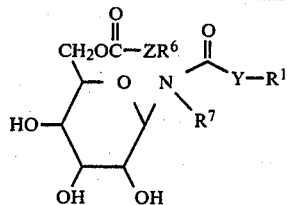

| Example No. | Sugar | Y | Z | $R^1$ | $R^6$ | $R^7$ | Rf (6:1 toluene/isopropanol) |
|---|---|---|---|---|---|---|---|
| (10) | Glucose | $CH_2$ | $CH_2$ | $(CH_2)_9CH_3$ | H | $(CH_2)_{17}CH_3$ | 0.35 |
| (11) | " | $CH_2$ | $CH_2$ | " | $(CH_2)_{15}CH_3$ | " | 0.39 |
| (12) | " | $CH_2$ | $CH_2$ | " | $OCH_2CH_2OC_4H_9-n$ | " | 0.35 |
| (13) | " | $CH_2$ | $CH_2$ | " | $(CH_2)_9CH_3$ | " | 0.36 |
| (14) | " | O | $CH_2$ | " | H | " | 0.35 |
| (15) | " | S | $CH_2$ | $(CH_2)_{17}CH_3$ | " | " | 0.34 |
| (16) | " | $CH_2$ | O | $(CH_2)_9CH_3$ | $CH_2CH_2OC_4H_9-n$ | " | |
| (17) | " | $CH_2$ | S | " | " | " | |
| (18) | Galactose | $CH_2$ | $CH_2$ | " | $OCH_2CH_2OC_4H_9-n$ | " | 0.36 |
| (19) | Mannose | $CH_2$ | $CH_2$ | " | " | " | 0.30 |
| (20) | Glucose | $CH_2$ | $CH_2$ | " | $OCH_3$ | " | 0.316 |
| (21) | " | $CH_2$ | $CH_2$ | " | $(OCH_2CH_2)_2OC_4H_9-n$ | " | 0.323 |
| (22) | " | $CH_2$ | $CH_2$ | " | $(OCH_2CH_2)_4OCH_3$ | " | 0.173 |
| (23) | " | $CH_2$ | O | " | $CH_2CH_2OCH_2CH_2OC_2H_5$ | " | 0.302 |
| (24) | Mannose | $CH_2$ | $CH_2$ | $(CH_2)_{15}CH_3$ | $OCH_2CH_2OC_4H_9-n$ | $(CH_2)_{13}CH_3$ | 0.32 |
| (25) | Galactose | $CH_2$ | $CH_2$ | " | " | $(CH_2)_{11}CH_3$ | 0.34 |

It will be understood that the specification and examples are illustrative but not limitative of the present invention and that other embodiments within the spirit and scope of the invention will suggest themselves to those skilled in the art.

What is claimed is:

1. A compound of the formula

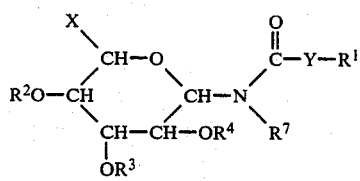

in which
X is hydrogen or the radical $-CH_2OR^5$,
three of $R^2$, $R^3$, $R^4$ and $R^5$ each independently is hydrogen or

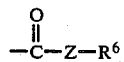

and the fourth is

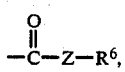

Y and Z each independently is oxygen, sulphur, NH or $CH_2$, and
$R^1$, $R^6$ and $R^7$ each independently is an optionally substituted hydrocarbon radical having up to 50 carbon atoms.

2. A compound according to claim 1, in which the hydrocarbon radicals of $R^1$, $R^6$ and $R^7$ contain up to 21 carbon atoms.

3. A compound according to claim 1, in which the hydrocarbon radicals of $R^1$, $R^6$ and $R^7$ contain 9–21 carbon atoms.

4. A compound according to claim 1, in which $R^2$, $R^3$ and $R^4$ are hydrogen and X is $CH_2OCOZR^6$, wherein Z and $R^6$ are as defined in claim 1.

5. A compound according to claim 1, which is N-octadecyl-N-dodecanoyl-(6-acetyl-β-D-glucopyranosyl)-amide of the formula

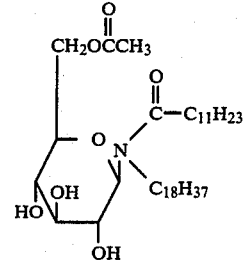

6. A compound according to claim 1, which is N-octadecyl-N-dodecanoyl-(6-[3,6-Dioxodecanoyl]-β-D-glucopyranosyl)-amide of the formula

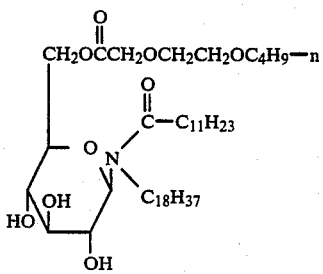

7. A compound according to claim 1, which is N-octadecyl-N-dodecanoyl-(6-[3,6-Dioxodecanoyl]-β-D-galactopyranosyl)-amide of the formula

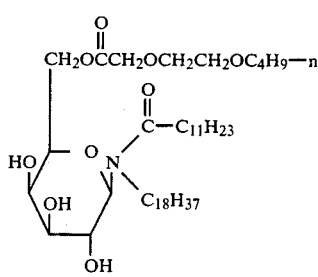

8. A compound according to claim 1, which is N-octadecyl-N-dodecanoyl-(6-[3,6-Dioxodecanoyl]-β-D-mannopyranosyl)-amide of the formula

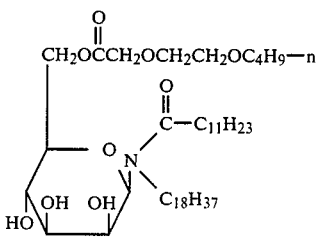

9. A compound according to claim 1, which is N-octadecyl-N-dodecanoyl-(6-methoxyacetyl-β-D-glucopyranosyl)-amide of the formula

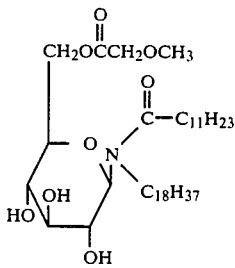

10. An immune system-stimulating composition comprising a pharmaceutically acceptable diluent and an immune system-activating amount of a compound according to claim 1.

11. A unit dose according to claim 10 in the form of a tablet, capsule or injectable solution.

12. A method of activating the immune system of a patient which comprises administering to a patient an amount effective therefor of a compound according to claim 1.

13. The method according to claim 12, wherein the compound is
   N-octadecyl-N-dodecanoyl-(6-acetyl-β-D-glucopyranosyl)-amide,
   N-octadecyl-N-dodecanoyl-(6[3,6-Dioxodecanoyl]-β-D-glucopyranosyl)-amide,
   N-octadecyl-N-dodecanoyl-(6-[3,6-Dioxodecanoyl]-β-D-galactopyranosyl)-amide,
   N-octadecyl-N-dodecanoyl-(6-[3,6-Dioxodecanoyl]-β-D-mannopyranosyl)-amido, or
   N-octadecyl-N-dodecanoyl-(6-methoxyacetyl-β-D-glucopyranosyl)-amide.

* * * * *